United States Patent [19]

Clark

[11] Patent Number: 5,720,738
[45] Date of Patent: Feb. 24, 1998

[54] EDGE-PROTECTED LAYERED ABSORBENT PRODUCTS

[75] Inventor: Tracey A. Clark, Highland Park, N.J.

[73] Assignee: McNeil-PPC, Inc., Skillman, N.J.

[21] Appl. No.: 550,485

[22] Filed: Oct. 30, 1995

[51] Int. Cl.[6] ........................................ A61F 13/15
[52] U.S. Cl. ...................... 604/385.1; 604/390; 604/387
[58] Field of Search ...................... 604/358, 607, 604/378, 385.1, 385.2, 365, 368, 386, 389, 390, 387

[56] References Cited

U.S. PATENT DOCUMENTS

| 2,929,379 | 3/1960 | Poulsen | 604/372 |
|---|---|---|---|
| 3,367,334 | 2/1968 | Testa | 604/370 |
| 3,570,492 | 3/1971 | Bettencourt . | |
| 4,019,517 | 4/1977 | Glassman | 604/397 |
| 4,022,210 | 5/1977 | Glassman . | |
| 4,072,150 | 2/1978 | Glassman . | |
| 4,405,310 | 9/1983 | Karami | 604/383 |
| 4,425,130 | 1/1984 | DesMarais | 604/385.2 |
| 4,505,707 | 3/1985 | Feeney . | |
| 4,576,597 | 3/1986 | Hlaban | 604/385.1 |
| 4,623,341 | 11/1986 | Roeder . | |
| 5,037,418 | 8/1991 | Kuns et al. | 604/385.1 |
| 5,429,631 | 7/1995 | Grenier | 604/385.1 |
| 5,599,339 | 2/1997 | Horney | 604/385.1 |

FOREIGN PATENT DOCUMENTS

| 0391727 | 10/1990 | European Pat. Off. | 604/378 |
|---|---|---|---|
| 1219906 | 5/1960 | France | 604/378 |
| 0175230 | 11/1985 | Japan . | |
| 5177 | 1/1993 | Japan . | |
| 0520576 | 4/1940 | United Kingdom | 604/385.1 |

*Primary Examiner*—Mark Polutta

[57] ABSTRACT

A multilayered absorbent feminine hygiene product which is configured for releasable attachment to an user's garment has a plurality of absorbent pads. Each of the absorbent pads has an absorbent layer to contain absorbed fluid and a barrier layer to prevent absorbed fluid from leaking completely through the individual pad. The pads are releasably attached along at least a portion of their lateral edges with a protective material. The protective material protects unexposed absorbent pad layers from soiling by fluid runoff from the exposed pad layer, and it contributes to the attachment strength between the layers during use.

6 Claims, 2 Drawing Sheets

EDGE-PROTECTED LAYERED ABSORBENT PRODUCTS

FIELD OF THE INVENTION

The present invention relates to a multilayered absorbent feminine hygiene product. In particular, it relates to a stacked or layered product containing individual absorbent pads which are releasably attached one to another along their lateral edges in a manner to protect unexposed absorbent pad layers.

BACKGROUND OF THE INVENTION

Absorbent products have long been used as feminine hygiene products. Discretion in the use of these products has been a goal of manufacturers and users alike. Absorbent pads and napkins used for feminine hygiene provide some specific capacity for absorbing body fluids. Once soiled, a product must be replaced by an unsoiled product. Unfortunately, a woman is not always at home or otherwise conveniently near a supply of these absorbent products, and it may be necessary for her to keep a minimal supply of products with her. Thus, feminine hygiene products have been manufactured to be carried conveniently in a woman's purse or pocketbook. These products have also been manufactured in convenient, individual packages to keep the product clean until use. However, more discrete ways to keep a ready supply of feminine hygiene products handy are constantly sought.

Poulsen, U.S. Pat. No. 2,929,379, suggested that a woman might carry a supply of three sanitary napkins in a belted sanitary napkin product having multiple layers. The belted nature of these sanitary napkins allow the napkins to be held closely to the user's body. The plurality of absorbent layers of the Poulsen product are stacked and attached in one general location in the anterior portion of the sanitary napkin product. The posterior portion of the individual layers are not anchored to adjacent layers. It is constrained only by the nature of the belted product. Thus, bodily fluids which are deposited on the exposed upper napkin may also soil lower layers if these layers shift outwards of the protecting upper layers.

In more recent times, belted feminine hygiene products have generally been replaced by products which are releasably secured to a user's undergarments by means of a layer or strip of pressure sensitive adhesive disposed upon a garment-facing surface of the product. In addition, new and thinner products, including thin sanitary napkins and panty liners, have been developed. Panty liners may be used for applications other than those for which traditional sanitary napkins were designed. These feminine hygiene products are substantially thinner than conventional sanitary napkins and have a substantially concentrated absorbent volume. Thin feminine hygiene products therefore, have less of the absorbent fluff layer which helps to provide flexibility to the product.

Most feminine hygiene products have a body-facing absorbent side and a garment facing barrier side. A pressure sensitive adhesive is generally disposed on the garment facing side as one or more lines to provide attachment means to removably fix the product to the garment. This pressure sensitive adhesive is protected from contamination until use with a piece of release liner. When the product is to be used, the user must first remove the release liner and dispose of it. The disposal of a piece of release liner with each panty liner increases the waste generated by the use of these products. Thus, it is desirable to reduce the amount of release liner used in conjunction with panty liners in an era of increased environmental awareness.

Absorbent products have a finite absorbent capacity, and they must be periodically replaced. Manufacturers continue to search for products which are easily carried by a user, are convenient and discrete. One solution is discussed in Takao et al., Japanese Utility Model 5-177 (Y2), which discloses a panty liner product having three single layers stacked and secured together. The bottom panty liner has a conventional adhesive disposed for positioning the product in the crotch area of a user's undergarment. Like Poulsen Takao fails to protect lower layers from staining, especially due to side leakage failure.

Additionally, Fuji Kikaku, Ltd. Japanese Utility Model Application No 60-175230 (U), discloses a multilayered sanitary napkin product having smaller pads stacked on top of larger pads and secured with two discrete strips of adhesive tape. Again, these strips are at the ends of the pad layers. This reference also fails to protect lower layers from leakage during use.

Therefore, a new and useful panty liner product is needed having a plurality of absorbent pads which are releasably attached together in a secure manner and which protect lower layers from premature soiling.

SUMMARY OF THE INVENTION

The present invention relates to an absorbent feminine hygiene product which is configured for releasable attachment to a user's garment. The product is formed of a plurality of stacked individual absorbent pads having longitudinal ends and lateral edges. Each pad has an absorbent structure having a first, liquid-permeable surface and a barrier disposed on a second surface, opposite the first, of the absorbent structure. The individual pads are releasably attached along at least a portion of their lateral edges. Thus, the flow of significant amounts of liquid from an exposed absorbent pad to another releasably attached pad during use is substantially prevented.

The invention also relates to a method of manufacturing such a product. In this method a plurality of individual absorbent pads are formed having longitudinal ends and lateral edges. The pads have an absorbent structure having a first, liquid-permeable surface and a barrier disposed on a second surface, opposite the first. The second or garment-facing surface of a first absorbent pad is configured for releasable attachment to a user's garment. A second absorbent pad is releasably attached to this first pad along at least a portion of their lateral edges in a manner to substantially prevent the flow of significant amounts of liquid from an exposed absorbent pad to the first absorbent pad during use.

DETAILED DESCRIPTION OF THE PREFERRED EMBODIMENT

Figure 1:
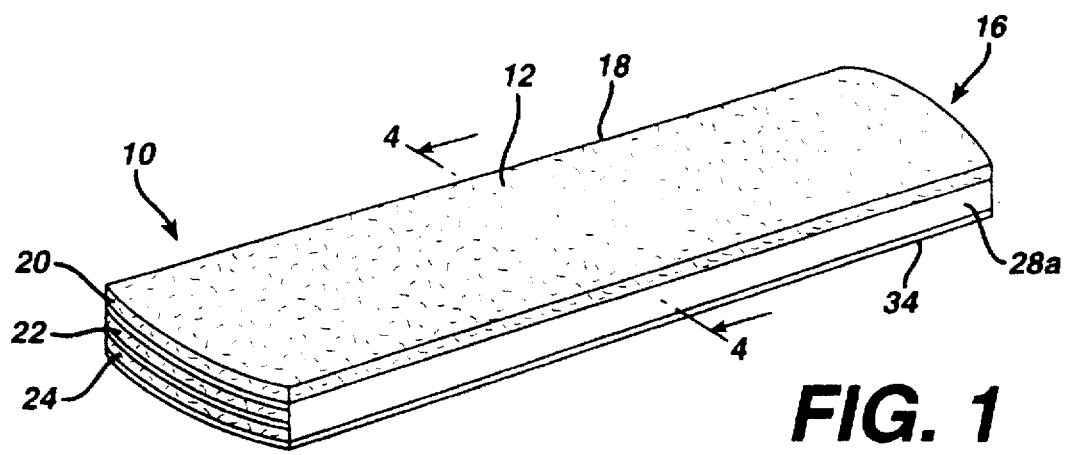
FIG. 1 shows a perspective view of a multilayered absorbent product according to one embodiment of the present invention.
Figure 2:
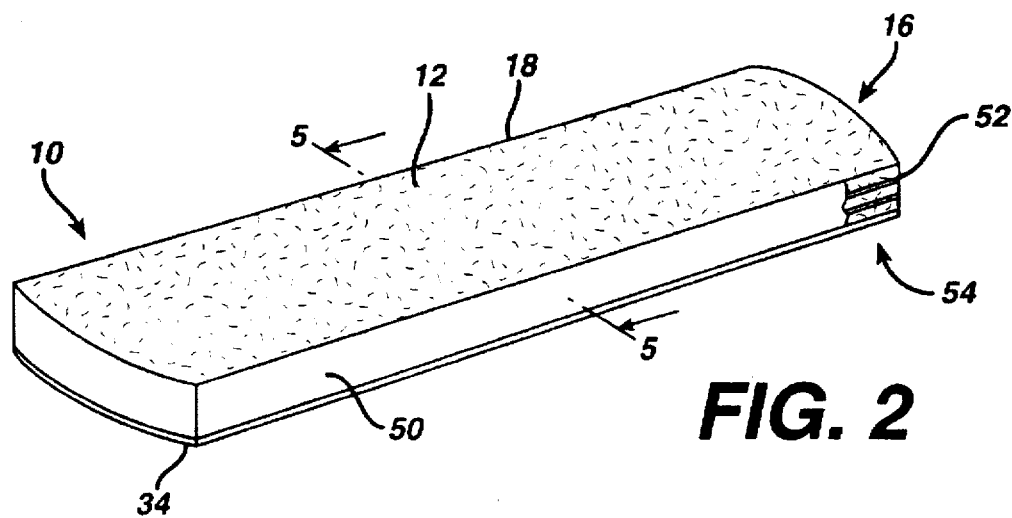
FIG. 2 shows a partially broken-away, perspective view of a multilayered absorbent product according to an alternative embodiment of the present invention.

The absorbent product of the present invention has a plurality of individual attached absorbent pads which are stacked together. The pads are releasably attached along at least a portion of their lateral edges. Thus, the flow of significant amounts of liquid from an exposed absorbent pad to another releasably attached pad during use is substantially prevented. Preferably, the attachment means continue to hold adjacent pads together under both shear and minimal peel forces likely to be encountered during product use.

The absorbent pads which are stacked in the absorbent product may be of any geometry normally used in the feminine hygiene field, including strip-like (See FIG. 1), dog-bone or hourglass shaped, and the like. Preferably, the pads are of substantially similar geometry, although they may have slightly different proportions. Thus, successive absorbent pads may be longer or shorter in length.

The individual absorbent pads of the multilayered product are preferably relatively thin. This allows several absorbent pads to form an absorbent product which will not be too thick for the average product user. The individual pads may be panty liners, thin sanitary napkins or even ultrathin sanitary napkins, and possibly thin incontinence pads. Preferably, the individual absorbent pads of the invention have a thickness of less than about 10 mm, more preferably, less than about 5 mm, and most preferably, less than about 2.5 mm.

The absorbent product of the present invention remains flexible. Indeed, preferred multilayered absorbent products have a flexural resistance in the range of equivalent absorbent products. Thus, multilayered sanitary napkins have a flexural resistance in the range of conventional sanitary napkins, and multilayered panty liners have a flexural resistance in the range of conventional panty liners. Examples of single layered panty liner products currently on the market include CAREFREE PANTY SHIELDS, KOTEX LIGHTDAYS PANTILINERS, NEW FREEDOM PANTILINERS, ALWAYS PANTILINERS and the like. Commercially available thin napkins include SURE & NATURAL THIN, ULTRA THIN, and PRIMA napkins, STAYFREE THIN and ULTRA THIN napkins, ALWAYS ULTRA napkins, and KOTEX ULTRA THIN napkins, etc.

Referring to FIGS. 1–6 wherein like numerals represent like elements, the absorbent product 10 has a plurality of individual absorbent pads. The absorbent product 10 is arranged to have a body-facing surface 12, a garment-facing surface 14, longitudinal ends 16, and lateral edges 18. While these illustrated embodiments include three individual pads: a top pad 20, a middle pad 22, and a bottom pad 24, one of ordinary skill in the art would recognize that fewer or more individual pads could be combined into an absorbent product 10. Each absorbent pad has at least an absorbent structure 26 and a barrier 28. Preferably, each absorbent product 10 has attaching means 30 on the garment-facing surface 14 for attaching the product to a user's garment.

The absorbent structure 26 may include several layers, or it may be a single layer having an upper liquid pervious surface. Preferably, the absorbent structure has several layers, the top layer forming the liquid pervious layer. The liquid permeable layer may be a nonwoven fabric such as a spunbonded fabric, a thermal bonded fabric, a resin bonded fabric, and the like; an apertured film such as DRI-WEAVE, RETICULON, and the like; a densified top layer formed with hydrogen bonding; or any other suitable covering surface. The rest of the absorbent structure 26 may be cellulosic fibers, including wood pulp and cotton pulp; synthetic fibers, including polyolefins and polyesters; and the like. Preferably, the absorbent structure includes wood fluff pulp and about 5 to 80% of fusible, thermoplastic fibers. Useful absorbent structures and top surfaces are disclosed in Cancian et al., U.S. Pat. No. 4,592,943; Mays, et al. U.S. Pat. No. 4,713,134; Mays U.S. Pat. No. 4,787,947 and Shimalla et al., U.S. Pat. No. 4,774,124. The disclosures of which are herein incorporated by reference.

The fibrous materials found to be satisfactory in the making of the liquid permeable layer have been found to be blends of two thermoplastic fibers having distinguishable melting temperatures. Bicomponent fibers, fibers with an inner core of a thermoplastic fiber, e.g., polyester, surrounded by an outer sheath of thermoplastic e.g., polyethylene, having a melting point much lower than the core, have been found to be the best fibers to work with from processing and performance standpoints in this class of absorbent pads. It is also conceivable that the material for liquid permeable layer may be coformed blends of pulp fluff and thermoplastic fibers, e.g., polypropylene.

The barrier 28 may be any barrier useful in the panty liner and sanitary napkin art. Useful barriers include, without limitation, polymeric films or coatings, such as polyolefins (e.g., polyethylene and polypropylene), polyvinyls (e.g., polyvinyl acetate, polyvinyl chloride, and polyvinylidene chloride), copolymers (e.g., ethylenevinyl acetate), and blends or laminates of one or more of the above polymers; bodily fluid-repellant structures such as nonwovens, apertured films, and repellant fiber layers integrated into the bottom layer of the absorbent structure such as disclosed in Bergquist et al., U.S. Ser. No. 07/498,071, herein incorporated by reference. Preferred barriers include ethylene-vinyl acetate/polyethylene laminate films, polypropylene films, and bodily fluid-repellant nonwovens, such as polypropylene.

The attachment means 30 may be any means useful for attaching the product 10 to the user's garment. Known attachment means include pressure sensitive adhesives, mechanical clips, hook-and-loop fasteners, frictional fasteners (e.g., foam, high-friction polymeric material, high denier fiber-based nonwovens), and the like. In the embodiments illustrated in the Figures, the attachment means 30 includes a pressure sensitive adhesive 32 which is protected until use by a release liner 34.

The releasable attachment between the individual pads 20, 22 and 24 to form the product 10 may extend about the entire periphery of the product 10, or it may extend about less than the entire periphery. For example, the releasable attachment may extend along the lateral edges 18 of the product 10, leaving the longitudinal ends 16 uncovered. As indicated above, the releasable attachment extends along at a portion of the lateral edges 18, preferably, a major portion, about the middle of the product 10 in the longitudinal direction. Most preferably, the releasable attachment extends along the majority of the periphery of the product 10, leaving only a portion of the longitudinal ends 16, or the corners 52 uncovered to provide a finger lift 54. Generally speaking, the greater proportion of the periphery which is attached, the greater the product integrity. Conversely, the lesser proportion of the periphery which is attached, the lesser the product integrity. Of course, this product integrity can be enhanced by incorporating additional interpad attachment means such as disclosed in the commonly assigned, copending application, U.S. Ser. No. 08/236,762, which is herein incorporated by reference. These additional interpad attachment means may be the dominant attachment mechanism.

Figure 4:
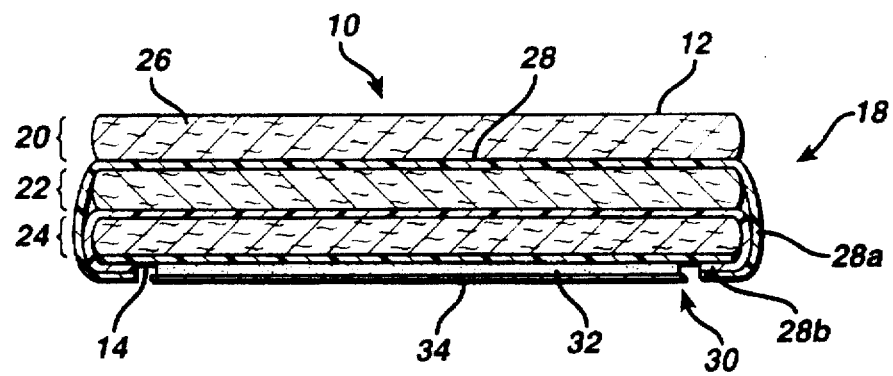
FIG. 4 shows a cross section along line 4—4 in FIG. 1.
Figure 5:
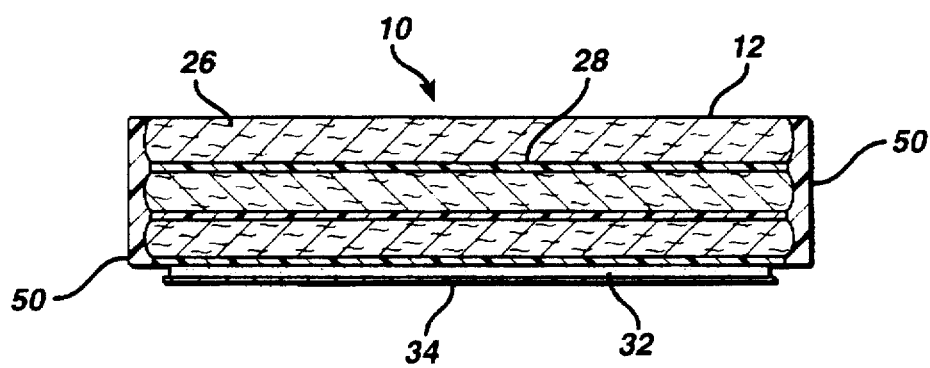
FIG. 5 shows a cross section along line 5—5 in FIG. 2.

In the embodiment of FIGS. 1 and 4, the individual pads 20, 22, and 24, are releasably attached along at least a portion of their lateral edges 18 by means of lateral barrier extensions 28a and 28b. These extend from the lateral edges 18 of the top and middle pads 22 and 24, respectively. The extension 28a of the top pad 12 encloses both the middle pad 22 and the bottom pad 24. However, it will be recognized that extension 28a may be releasably attached to extension 28b in a manner to enclose only the middle pad 22. The extension 28b of the middle pad 22 encloses only the bottom pad 24. The middle pad extension 28b is releasably attached to the barrier 28 of the bottom pad 24. The top pad extension 28a may be releasably attached to barrier 28 of the bottom pad 24 or to the middle pad extension 28b proximate its attachment to the barrier 28 of the bottom pad 24. The releasable nature of the attachment of the extensions 28a and 28b may be achieved through the weakening of these extensions proximate their attachment points to provide a predetermined severing location. It may also be achieved by releasable bonds among the extensions 28a and 28b and the barrier 28.

In the embodiments of FIGS. 2, 3, 5 and 6, the individual pads 20, 22, and 24, are releasably attached together along at least a portion of their lateral edges 18 by means of protective material 50.

Preferably, the protective material 50 is a frangible, substantially bodily fluid-repellant material which forms a non-tacky, flexible, cohesive structure. The structure may be, without limitation, selected from webs, coatings, and/or films. A representative, non-limiting list of useful webs includes in situ-formed fibrous webs (e.g., melt-blown, spunbonded, etc.), nonwoven tapes, tissues, and the like. A representative, non-limiting list of useful coatings and films includes foams, gels, adhesives, rubbers, other polymeric coatings and/or films, and the like. Preferred protective materials 50 include silicone gels, natural or synthetic rubbers, flexible plastics, foams, melt-blown fibers.

The protective material 50 performs at least two functions: it protects unexposed absorbent pad layers from soiling by fluid runoff from the exposed pad layer, and it contributes to the attachment strength between the layers during use. The protective material 50 may provide its protection by forming a complete liquid barrier, such as a sealant, or by being sufficiently bodily-fluid repellant to cause runoff liquids to bypass the protected layers. The protective material 50 has sufficient cohesive strength to prevent premature separation of the absorbent pad layers during use, so the material maintains its protective function. If there is no additional interpad attachment means, the protective material should have sufficient strength to hold the pad layers together. However, if additional interpad attachment means are used, the protective material 50 minimally requires sufficient cohesive strength to hold the pad edges together.

Figure 3:
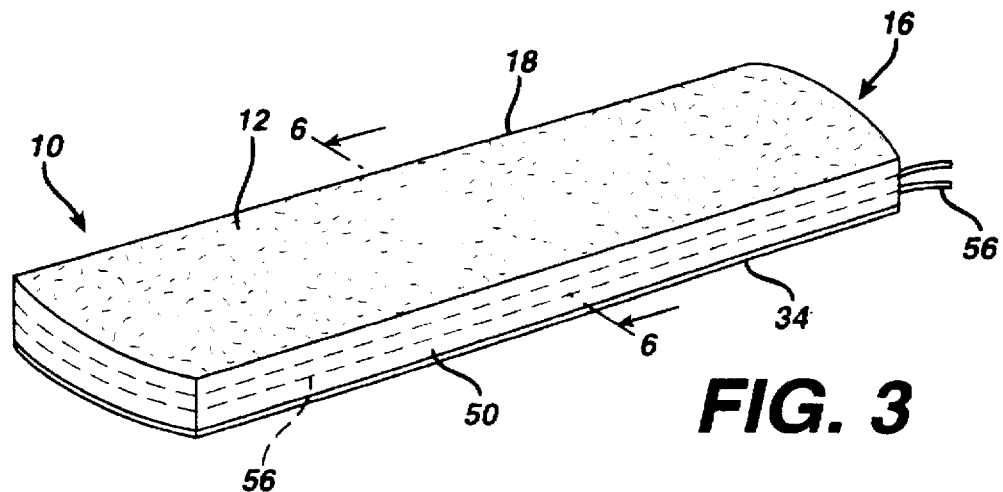
FIG. 3 shows a perspective view of a multilayered absorbent product according to another alternative embodiment of the present invention.
Figure 6:
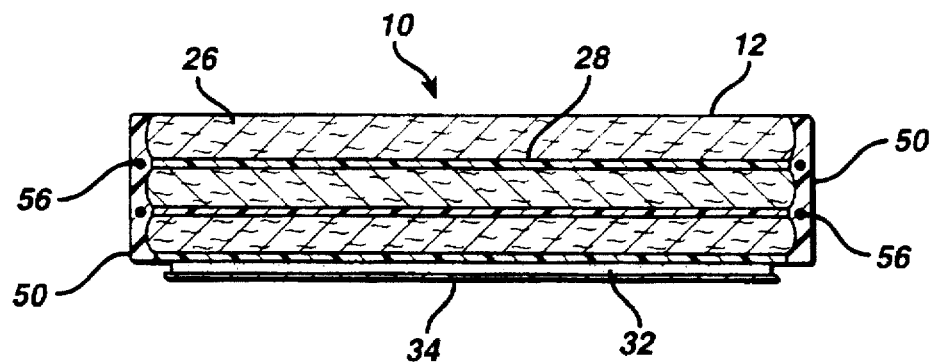
FIG. 6 shows a cross section along line 6-6 in FIG. 3.

In the embodiment of FIGS. 3 and 6, the finger lift 54 is replaced by an embedded severing means, such as a release strip 56. Useful severing means include strings, threads, filaments, polymeric tapes including polytetrafluoroethylene (PTFE), wires, and the like.

The product 10 can be formed by manufacturing a plurality of individual absorbent pads 20, 22, and 24. The manufacture of these pads is known by those of ordinary skill in the art. Indeed these pads can be identical to those panty liners and thin sanitary napkins currently on the market which are identified above. The second or garment-facing surface 14 of a first absorbent pad 24 is configured for releasable attachment to a user's garment. Subsequent absorbent pads 20 and 22 are stacked on the first pad wherein the liquid-permeable surface of one pad faces the garment-facing surface of an adjacent pad. At least a portion of the individual pad's lateral edges 18 are protected in a manner to substantially prevent the flow of significant amounts of liquid from an exposed absorbent pad 20 to the first absorbent pad 24 during use.

In the embodiment of FIGS. 1 and 4, the lateral edges 18 are protected by wrapping an extended barrier layer 28a and 28b of upper absorbent pads 20 and 22 around lower absorbent pads. The extended barrier layers 28a and 28b and the barrier 28 of the bottom pad 24 are releasably attached to each other. In the embodiments of FIGS. 2, 3, 5, and 6, at least the lateral edges 18 of stacked absorbent pads 20, 22, and 24 may be coated with a flowable protective material 50. In particular, the protective material 50 may be sprayed, brushed, printed, roll coated, transfer coated, or otherwise applied to the periphery of the product in a flowable form (e.g., liquid) and allowed to dry or cure to form the necessary flexible, bodily fluid-impermeable cohesive mass and/or film. In order to locate the protective material 50 only along the periphery of the product 10, the uncoated surfaces may be masked. The release strip 56 may be embedded into the protective material 50 by applying it to the periphery between adjacent, stacked pads during the application of the protective material 50 or shortly thereafter when the protective material 50 remains sufficiently flowable to permit the release strip 56 to penetrate into the protective material 50. In addition, the protective material 50 may be applied in two steps separated by the addition of the release strip 56.

The present invention also contemplates the application of the protective material 50 in the form of a fibrous web a film or a tape. Those of ordinary skill in the art will recognize that these may be applied with adhesives, or they may be applied in a tacky state.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent feminine hygiene product which is configured for releasable attachment to a user's garment, the product comprising a) a plurality of stacked individual absorbent pads, each pad comprising an absorbent structure having a first, liquid-permeable surface and a barrier layer disposed on a second surface, opposite the first, of the absorbent structure and having a periphery, longitudinal ends and lateral sides extending from the liquid-permeable surface to the second surface, and b) frangible means for releasably attaching the individual pads together comprising a substantially bodily fluid-repellent material disposed on the lateral sides thereof whereby the flow of significant amounts of liquid from an exposed absorbent pad to another releasably attached pad during use is substantially prevented.

2. The product of claim 1 wherein a first, garment-facing absorbent pad further comprises garment-attaching means.

3. The product of claim 1 wherein the attaching means comprises a lateral extension of the barrier layer of a second absorbent pad which lateral extension extends toward and is releasably attached to the barrier layer of the first, garment-facing pad.

4. The product of claim 1 wherein the body fluid-repellant material further comprises means for severing the protective material between adjacent pads.

5. The product of claim 1 wherein the bodily fluid-repellant material is disposed along at least a major portion of a central portion of the lateral sides of the pads.

6. The product of claim 5 wherein the bodily fluid-repellant material is disposed along at least a major portion of the longitudinal ends and lateral sides of the pads.

* * * * *